United States Patent
Yang

(10) Patent No.: US 10,829,399 B2
(45) Date of Patent: Nov. 10, 2020

(54) ANAEROBIC REACTOR

(71) Applicant: WOXFORD ENVIRONMENTAL TECHNOLOGIES (UK) LTD., Oxford (GB)

(72) Inventor: Ke Yang, Oxford (GB)

(73) Assignee: WOXFORD ENVIRONMENTAL TECHNOLOGIES (UK) LTD., Oxford (GB)

( * ) Notice: Subject to any disclaimer, the term of this patent is extended or adjusted under 35 U.S.C. 154(b) by 0 days.

(21) Appl. No.: 16/307,207

(22) PCT Filed: Jun. 13, 2017

(86) PCT No.: PCT/GB2017/051707
§ 371 (c)(1),
(2) Date: Dec. 5, 2018

(87) PCT Pub. No.: WO2017/216534
PCT Pub. Date: Dec. 21, 2017

(65) Prior Publication Data
US 2019/0263694 A1    Aug. 29, 2019

(30) Foreign Application Priority Data

Jun. 13, 2016  (GB) .................................. 1610271.7

(51) Int. Cl.
*C02F 3/28* (2006.01)
*C02F 103/34* (2006.01)
(Continued)

(52) U.S. Cl.
CPC .......... *C02F 3/2846* (2013.01); *C02F 3/2873* (2013.01); *C12M 21/04* (2013.01);
(Continued)

(58) Field of Classification Search
CPC ............................. C02F 3/2846; C02F 3/2873
(Continued)

(56) References Cited

U.S. PATENT DOCUMENTS 5,441,634 A * 8/1995 Edwards ............... C02F 3/1284
    210/194
5,688,400 A   11/1997 Baxter, Sr.
(Continued)

FOREIGN PATENT DOCUMENTS

AU    2014200009 A1    7/2014
CN    101054234 A      10/2007
(Continued)

OTHER PUBLICATIONS

Hu et al, CN 102491511, machine translation, pp. 1-6 (Year: 2012).*
(Continued)

*Primary Examiner* — Claire A Norris
(74) *Attorney, Agent, or Firm* — Withrow & Terranova, P.L.L.C.; Vincent K. Gustafson

(57) ABSTRACT

An anaerobic reactor (1) for treating waste water includes a reaction vessel (2) and a three phase separator (4) above the reaction vessel and arranged to receive effluent from the reaction vessel. The three phase separator includes an outer wall (10, 14) connected at its bottom to the top of the reaction vessel and a liquid outlet (42), a lid (16) closing the top of the outer wall. The lid has a gas outlet (17) above the level of the liquid outlet. The three phase separator also includes a funnel (18) arranged above the reaction vessel, a guide wall (30) spaced from and arranged radially outward of the funnel so to surround an upper aperture of the funnel and a baffle wall (36) spaced from and arranged between the guide wall and the liquid outlet.

15 Claims, 5 Drawing Sheets

(51) Int. Cl.
*C12M 1/107* (2006.01)
*C12M 1/00* (2006.01)
*C12M 1/08* (2006.01)
*C12M 1/26* (2006.01)

(52) U.S. Cl.
CPC ............ *C12M 23/02* (2013.01); *C12M 27/20* (2013.01); *C12M 27/24* (2013.01); *C12M 33/22* (2013.01); *C02F 2103/343* (2013.01); *C02F 2203/006* (2013.01); *C02F 2301/028* (2013.01)

(58) Field of Classification Search
USPC .......................... 210/220, 150, 151, 188, 513
See application file for complete search history.

(56) References Cited

U.S. PATENT DOCUMENTS

2012/0067800 A1 3/2012 Kwon et al.
2012/0138527 A1 6/2012 Ren et al.

FOREIGN PATENT DOCUMENTS

| CN | 201056518 | Y | 5/2008 |
|---|---|---|---|
| CN | 101613153 | A | 12/2009 |
| CN | 102001748 | A | 4/2011 |
| CN | 201850177 | U | 6/2011 |
| CN | 202164213 | U | 3/2012 |
| CN | 102491511 | A | 6/2012 |
| CN | 102643693 | A | 8/2012 |
| CN | 202542948 | U | 11/2012 |
| CN | 202643424 | U | 1/2013 |
| CN | 203256027 | U | 10/2013 |
| CN | 203582582 | U | 5/2014 |
| CN | 203668109 | U | 6/2014 |
| CN | 204325084 | U | 5/2015 |
| DE | 10314933 | A1 | 10/2004 |
| JP | 2001259681 | A | 9/2001 |
| JP | 2001269694 | A | 10/2001 |
| JP | 2014184382 | A | 10/2014 |
| WO | 2010071417 | A2 | 6/2010 |

OTHER PUBLICATIONS

Search Report for United Kingdom Patent Application No. GB1610271.7, dated Nov. 28, 2016, 3 pages.

International Search Report and Written Opinion for International Patent Application No. PCT/GB2017/051707, dated Aug. 22, 2017, 16 pages.

International Preliminary Report on Patentability for International Patent Application No. PCT/GB2017/051707, dated Dec. 27, 2018, 10 pages.

* cited by examiner

ANAEROBIC REACTOR

This application is a 35 U.S.C. § 371 national phase filing of International Application No. PCT/GB2017/051707 filed on Jun. 13, 2017, and claims the benefit of United Kingdom Patent Application No. 1610271.7 filed on Jun. 13, 2016, wherein the disclosures of the foregoing applications are hereby incorporated by reference herein in their respective entireties.

This invention relates to an anaerobic reactor for treating waste water, in particular to an up-flow anaerobic sludge blanket reactor.

Anaerobic reactors, e.g. up-flow anaerobic sludge blanket (UASB) reactors, treat waste water (e.g. produced in chemical and pharmaceutical industries) by anaerobically digesting organic matter in the waste water input into the reactor (the influent) using anaerobic micro-organisms that degrade the organic material. This produces an effluent of the reaction products containing, inter alia, methane ($CH_4$), carbon dioxide ($CO_2$), water ($H_2O$) and residual solid (e.g. organic) matter ("sludge").

The digestion process generates a large number of small gas bubbles that coalesce as they rise up through the reactor. These growing bubbles, along with the flow of the liquid through the reactor, convey the (e.g. biomass) solids (sludge) produced upwards within the reactor. However, the sludge flocculates and/or granulates into larger agglomerations which then settle by gravity back down through the reactor. In a UASB reactor, the balance of the upward flow of liquid and bubbles, and the downward flow of flocculated and/or granulated sludge creates a layer ("blanket") of sludge in the reactor through which the influent flows.

In order that the gas (e.g. biogas) and the liquid (e.g. water) in the effluent can be output in good quality for useful purposes, and the sludge can be returned to the main body of the reactor to help with further anaerobic digestion, flocculation and/or granulation, such anaerobic reactors include a three phase separator, e.g. as shown in CN 101054234 A, that acts to separate the solid, liquid and gas components in the effluent from each other, with the liquid and gas components being tapped off from the reactor via respective outlets. This results in output liquid and gas that is each substantially free from sludge.

It is an aim of the invention to provide an improved anaerobic reactor.

When viewed from a first aspect the invention provides an anaerobic reactor comprising:
   a reaction vessel comprising an inlet for supplying influent to be treated into the reaction vessel, wherein the reaction vessel is arranged to treat the influent received from the inlet using anaerobic digestion;
   a three phase separator arranged above, and in fluid communication with, the reaction vessel, wherein the separator is arranged to receive effluent from the reaction vessel, wherein the effluent comprises solids, liquid and gas;
   wherein the three phase separator comprises:
      an outer wall connected at its bottom to the top of the reaction vessel;
      a liquid outlet;
      a lid closing the top of the outer wall, wherein the lid comprises a gas outlet above the level of the liquid outlet;
      a funnel arranged above, and in fluid communication with, the reaction vessel, wherein the funnel comprises a lower aperture proximal to the reaction vessel and an upper aperture distal from the reaction vessel, wherein the lower aperture and the outer wall of the separator and/or the top of the reaction vessel define an annular conduit therebetween, and the lower aperture has a cross sectional area that is greater than a cross sectional area of the upper aperture, and wherein the funnel comprises a wall extending between the lower aperture and the upper aperture and is arranged to receive effluent from the reaction vessel and to guide the effluent from the lower aperture to the upper aperture, wherein the upper aperture is arranged below the level of the liquid outlet and the annular conduit is arranged to allow solids in the effluent to pass therethrough and fall back into the reaction vessel;
      a guide wall spaced from and arranged radially outward of the funnel so to surround the upper aperture of the funnel, wherein the bottom of the guide wall defines a lower annular aperture between the bottom of the guide wall and the wall of the funnel and an upper aperture arranged above the upper aperture of the funnel, wherein the guide wall is arranged to guide gas in the effluent from the funnel through the upper aperture of the guide wall towards the gas outlet, and the guide wall is arranged to allow solids and liquids in the effluent to pass through the lower annular aperture; and
      a baffle wall spaced from and arranged between the guide wall and the liquid outlet, wherein the bottom of the baffle wall defines a lower aperture below the level of the liquid outlet and the top of the baffle wall defines an upper aperture above the level of the liquid outlet.

The present invention provides an anaerobic, e.g. UASB, reactor that includes a reaction vessel into which the influent to be treated is supplied through an inlet. The influent is treated using anaerobic digestion (and thus preferably, in use, the reaction vessel contains anaerobic (micro-)organisms). Above the reaction vessel and arranged to receive the treated effluent (containing solids, liquid and gas) from the reaction vessel, is positioned a three phase separator. The three phase separator acts to separate the solids, liquid and gas from each, with the three phase separator including a liquid outlet for outputting liquid from the reactor and a gas outlet for outputting gas from the reactor.

The three phase separator has an outer wall that is connected at its bottom to the top of the reaction vessel (such that the reaction vessel and the three phase separator together form an enclosed volume). A lid on top of the outer wall closes the top of the outer wall and thus defines the three phase separator part of the enclosed volume. The lid includes the gas outlet which is positioned above the level of the liquid outlet.

The three phase separator also includes a funnel (e.g. arranged within the enclosed volume of the three phase separator) that is positioned above the reaction vessel. The funnel is in fluid communication with the top of the reaction vessel such that it receives the effluent produced in the reaction vessel. The funnel has a wall that extends between a larger lower aperture (positioned closer to and above the top of the reaction vessel) and a smaller upper aperture (positioned closer to the lid). The wall is configured to receive the effluent from the reaction vessel and to guide it through the funnel to the upper aperture.

The (e.g. edge of the wall of the funnel forming the) lower aperture is spaced from the outer wall of the three phase separator and/or the top of the reaction vessel (e.g. at the point these two parts connect to each other), and positioned such that together they form an annular conduit therebetween. This annular conduit allows solids in the effluent (e.g. that have passed up through the middle of the funnel and out of the upper aperture) to pass back down into the reaction vessel.

The three phase separator also includes a guide wall configured to guide gas in the effluent from the funnel towards the gas outlet. The guide wall is spaced away from (radially outward of) the funnel so to surround the upper aperture of the funnel. A lower annular aperture is defined between the bottom of the guide wall and the outside of the wall of the funnel. The lower annular aperture is configured to allow solids and liquids in the effluent to pass therethrough, e.g. so that solids may then fall down towards the annular conduit defined by the funnel and the liquid can flow towards the outlet.

The top of the guide wall defines an upper aperture positioned above the funnel's upper aperture. The guide wall is configured to guide gas in the effluent that has flowed through the funnel through the upper aperture of the guide wall towards the gas outlet.

The three phase separator also includes a baffle wall that is positioned between (and spaced from both) the guide wall and the liquid outlet. The baffle wall extends both above and below the level of the liquid outlet between lower and upper apertures.

It will be appreciated that the anaerobic reactor of the present invention has lid that covers and closes the whole of the three phase separator, e.g. such that the anaerobic reactor (comprising the reaction vessel and the three phase separator) is a completely closed volume apart from the liquid inlet, the liquid outlet and the gas outlet. Providing a lid over the whole of the three phase separator maximises the gas in the effluent that is captured and thus able to be output through the gas outlet, and thus minimises the gas that escapes from the reactor, e.g. into the atmosphere. This contrasts with the UASB reactor disclosed in CN 101054234 A in which only the central part leading from the funnel is covered with a gas hood, thus leaving the volume through which the separated liquid and solids return open.

The Applicant has appreciated that in this volume of liquid and solids that has been separated from the majority of the gas in the effluent, gas is likely to continue to be released from the mixture of liquid and solids, e.g. owing to continuing anaerobic digestion. By providing, in the present invention, a lid over the entire three phase separator, all of the gas from the effluent is able to be captured.

However, when the whole of the three phase separator is covered, solids (e.g. sludge) are able to pass up towards the gas outlet (the level to which they are able to reach is preferably set by the level of the liquid outlet). In the UASB reactor disclosed in CN 101054234 A this was not possible owing to the gas pressure in the central hood part preventing the up-flow of liquid and solids above a particular level once the effluent had passed up through the funnel.

Therefore, as solids may pass then towards the liquid outlet, e.g. after spilling over the top of the guide wall, the Applicant has appreciated that by providing a baffle wall that is positioned between (and spaced from both) the guide wall and the liquid outlet, solids are substantially prevented from contaminating the liquid output from the reactor, e.g. the baffle wall encourages the solids to flocculate and/or granulate, and fall back down through the three phase separator and into the reaction vessel.

The reactor may be any suitable and desired type of anaerobic reactor. Preferably the reactor is an up-flow anaerobic sludge blanket (UASB) reactor.

The reaction vessel may be configured in any suitable and desired way for treating the influent from the inlet using anaerobic digestion. Preferably the reaction vessel comprises a cylindrical body, e.g. having a circular cross section. Preferably the influent inlet is provided towards the bottom of the reaction vessel, e.g. such that the influent is arranged to flow up through the reaction vessel while being treated.

In use, preferably the reaction vessel is arranged such that the anaerobic digestion process generates a large number of small gas bubbles that coalesce as they rise up through the reactor. Thus, in use, preferably the reaction vessel contains anaerobic (micro-)organisms for performing the anaerobic digestion. These growing bubbles, along with the flow of the liquid through the reactor, preferably convey the solids (sludge) produced upwards within the reactor. However, the sludge flocculates and/or granulates into larger agglomerations which then settle by gravity back down through the reactor.

It will be appreciated over time that the anaerobic (micro-)organisms breed and thus the volume of sludge will grow to create, in at least preferred embodiments, e.g. in a UASB reactor, a "blanket" of sludge. In a UASB reactor, the balance of the upward flow of liquid and bubbles, and the downward flow of flocculated and/or granulated sludge creates a stable layer ("blanket") of sludge in the reactor through which the influent flows.

Thus the anaerobic reactor may be arranged to operate in any suitable and desired way. The anaerobic reactor may be arranged to operate to produce granular and/or flocculated sludge. However, in a preferred embodiment, in operation the anaerobic reactor is arranged to produce predominantly granular sludge. The anaerobic reactor may be operated to produce predominantly granular sludge in any suitable and desired way. There may also be a start-up period during which the anaerobic reactor produces some flocculated sludge (e.g. owing to the reaction vessel having been seeded with flocculated sludge), however preferably after this start-up period, the anaerobic reactor produces predominantly granular sludge. Then, preferably as long as the anaerobic reactor is operated as instructed, according to a predefined set of control parameters, the reactor will produce predominantly granular sludge in subsequent operation.

The influent may be any suitable and desired influent for treating anaerobically. In a preferred embodiment the influent comprises (waste) water, e.g. produced in chemical and pharmaceutical industries. Preferably the waste water contains, and thus the influent also comprises, organic matter (that the reactor is arranged to digest anaerobically).

The effluent produced in the reaction vessel through the anaerobic digestion of the influent may comprise any suitable and desired components. In a preferred embodiment the effluent comprises one or more (and preferably all) of: methane ($CH_4$), carbon dioxide ($CO_2$), water ($H_2O$) and residual solid (e.g. organic) matter ("sludge"). Thus preferably the reaction vessel is arranged to anaerobically digest the influent to produce these components.

The three phase separator, arranged to receive the effluent from the reaction vessel, may be provided in any suitable and desired way. In a preferred embodiment the reaction vessel has an open top that is covered by the three phase separator, e.g. the outer wall of the three phase separator is a continuous extension of the outer wall of the reaction vessel.

Preferably the three phase separator has an upper portion that is wider (e.g. has a greater diameter) than the reaction vessel. Thus preferably the outer wall of the three phase separator projects outwards from the top of the reaction vessel, e.g. at an obtuse outer angle from the wall of the reaction vessel. Thus preferably the three phase separator has a conical lower portion. Preferably the upper portion of the three phase separator is cylindrical, e.g. with a circular cross section.

Preferably the bottom of the three phase separator, e.g. an extension of the conical outer wall, projects into the interior of the reaction vessel.

The three phase separator is arranged to separate the gas, liquid and solid components of the effluent from each other. The three phase separator is thus arranged to output gas from the gas outlet, liquid from the liquid outlet and to return the solids to the reaction vessel (where they may contribute to the further anaerobic digestion of the influent, e.g. through the formation of a sludge blanket).

The liquid outlet may be arranged in the three phase separator in any suitable and desired way. In a preferred embodiment the liquid outlet is arranged to set a liquid level in (e.g. across the whole of) the three phase separator. Also, preferably the anaerobic reactor comprises a pressure control device in fluid communication with the gas outlet, e.g. to maintain a gas pressure inside the three phase separator, as will be discussed in more detail below. Thus preferably the pressure control device and the liquid outlet are arranged to set a liquid level in (e.g. across the whole of) the three phase separator, e.g. based on the pressure balance between the liquid rising up through the reaction vessel into the three phase separator and the gas pressure in the three phase separator.

The liquid outlet may be defined in the outer wall of the three phase separator, e.g. such that the liquid passes through the liquid outlet when the liquid level reaches the liquid outlet (e.g. against the pressure of the gas above the liquid). However, in a preferred embodiment the liquid outlet comprises a wall between the baffle wall and the outer wall of the three phase separator, e.g. creating a trough into which the liquid from the effluent flows. Thus preferably the top of the liquid outlet wall is arranged to set the liquid level in the three phase separator, e.g. such that liquid to be output from the three phase separator is arranged to spill over the top of the liquid outlet wall when the liquid level reaches the top of the liquid outlet wall (e.g. against the pressure of the gas above the liquid), e.g. and into the trough, from where it can be output.

Preferably the trough comprises a drain through which liquid is arranged to flow out of the trough. Preferably the liquid outlet wall (and thus the trough) extends substantially all the way around the perimeter (e.g. circumference) of the three phase separator, e.g. preferably the trough is continuous. Thus preferably the liquid outlet wall comprises a ring, e.g. a cylinder extending vertically.

The liquid outlet wall may be arranged relative to the baffle wall in any suitable and desired configuration. In a preferred embodiment the top of the liquid outlet wall is lower than the top of the baffle wall. Thus preferably the baffle wall prevents liquid (and solids) in the effluent from spilling over its top and thus passing straight into the liquid outlet. Preferably the baffle wall and the liquid outlet wall are arranged to form an annular flow path towards the liquid outlet, e.g. such that liquid in the effluent has to flow under the bottom of the baffle wall (thus encouraging solids to flocculate and/or granulate, and fall back down towards the reaction vessel) and then up and over the liquid outlet wall.

Preferably the liquid outlet comprises a trap (e.g. a U-bend) arranged to prevent gas from escaping through the liquid outlet. Preferably the trap is arranged downstream of the liquid outlet wall, e.g. downstream of the trough.

In order to control the flow of liquid out of the liquid outlet, the liquid outlet may comprise an arrangement (e.g. a valve) to control the flow of liquid therethrough (or the pressure of the liquid flowing therethrough). However preferably the liquid outlet is arranged, e.g. without having a restriction to the flow of liquid therethrough, to allow the liquid level in the three phase separator to be set (e.g. only) by the level of the liquid outlet (e.g. as long as the pressure of the liquid rising up through the reaction vessel and into the three phase separator is greater than the gas pressure in the three phase separator). Thus preferably the liquid outlet defines the maximum level of the liquid in the three phase separator. Preferably the liquid flowing up through the reactor is allowed to simply flow through the liquid outlet (e.g. over the liquid outlet wall) without restriction (e.g. as long as the pressure of the liquid rising up through the reaction vessel and into the three phase separator is greater than the gas pressure in the three phase separator).

Similarly, in order to control the flow of gas out of the gas outlet, the gas outlet may comprise an arrangement (e.g. a valve) to control the flow of gas therethrough (or the pressure of the gas flowing therethrough). Preferably, as indicated above, the anaerobic reactor comprises a pressure control device in fluid communication with the gas outlet, e.g. to create a back pressure of gas inside the three phase separator (along with the new gas being released from the effluent into the three phase separator). The pressure control device may be located, e.g. as a valve, in the gas outlet. However preferably the gas outlet is arranged without a restriction to the flow of gas therethrough (other than the cross sectional area of the gas outlet) to allow the gas in the three phase separator to flow out under the influence of the gas pressure in the three phase separator, e.g. as set by the pressure control device. Thus preferably the pressure control device is provided downstream from the gas outlet.

The pressure control device may comprise any suitable and desired device, e.g. a restriction, to maintain a gas pressure in the three phase separator. Preferably the pressure control device comprises a water sealing tank. The pressure control device may be arranged to maintain any suitable and desired gas pressure in the anaerobic reactor, e.g. in the three phase separator. Preferably the pressure control device is arranged to maintain a gas pressure above atmospheric pressure in the three phase separator. This helps to aid the flow of gas through the gas outlet.

The lid, that closes the top of the outer wall of the three phase separator, may be provided, e.g. attached to the outer wall of the three phase separator, in any suitable and desired way. Preferably, as with the body of the reaction vessel being continuous with the outer wall of the three phase separator, preferably the outer wall of the three phase separator is continuous with the lid. Thus preferably the lid substantially seals the three phase separator, e.g. other than the gas and/or liquid outlets.

The lid may be any suitable and desired shape, e.g. flat. However preferably the lid comprises a dome, e.g. having a convex outer wall. The gas outlet may be provided at any suitable and desired position in the lid. Preferably the gas outlet is in the centre of the lid, e.g. at the top of the dome. This enables the gas outlet to be provided as high as possible in the three phase separator.

The funnel may be arranged in the three phase separator in any suitable and desired way to be able to receive effluent from the reaction vessel and to guide the effluent up through the funnel. Preferably the (wall of the) funnel comprises a conical lower portion, e.g. extending up from the lower aperture, and a cylindrical upper portion, e.g. extending down from the upper aperture. Preferably the funnel is rotationally symmetric. Preferably the axis of rotation of the funnel is coaxial with the axis of rotation of the cylindrical reaction vessel.

The lower aperture of the funnel is preferably wider than, e.g. overhangs, the bottom of the outer wall of the three phase separator, e.g. the projection of the bottom of the three phase separator into the reaction vessel. This arrangement helps the lower aperture of the funnel to receive as much of the effluent of possible from the reaction vessel and helps to control the return of sludge to the reaction vessel through the annular conduit defined between the wall of the three phase separator and the lower aperture of the funnel.

The guide wall may be arranged in the three phase separator in any suitable and desired way to be able to guide gas in the effluent from the funnel towards the gas outlet and to allow solids and liquids in the effluent to pass through the lower annular aperture formed between the top of the funnel and the bottom of the guide wall. Preferably the guide wall is cylindrical, e.g. having a circular cross section. Preferably the guide wall extends vertically. Preferably the axis of rotation of the cylindrical guide wall is coaxial with the axis of rotation of the reaction vessel and/or the funnel.

Preferably the, e.g. cylindrical, e.g. lower portion of the, guide wall overlaps the cylindrical upper portion of the funnel. Thus preferably the lower annular aperture extends along the length of the cylindrical upper portion of the funnel.

The upper aperture of the guide wall (i.e. the top of the guide wall), that is arranged above the upper aperture of the funnel (i.e. the top of the funnel), is preferably also arranged above the level of the liquid outlet. Thus, in use, preferably the upper aperture of the guide wall is arranged to be above the level of the liquid in the three phase separator. Preferably the upper aperture of the guide wall is arranged at the same level as the top of the baffle wall. Thus preferably the guide wall is arranged to prevent the flow of liquid and solids in the effluent from passing over the top of the upper aperture of the guide wall.

The baffle wall, that is arranged to extend above and below the level of the liquid outlet, may be arranged in the three phase separator in any suitable and desired way. In use, preferably the top of the baffle wall (i.e. the upper aperture of the baffle wall) is higher than the liquid level in the three phase separator. Preferably the baffle wall is positioned proximal to the outer wall of the three phase separator, e.g. closer to the outer wall of the three phase separator than to the guide wall. This helps to minimise the volume of solids that pass into the liquid outlet.

Preferably the baffle wall is cylindrical, e.g. having a circular cross section. Preferably the baffle wall extends vertically. Preferably the axis of rotation of the cylindrical baffle wall is coaxial with the axis of rotation of the reaction vessel and/or the funnel and/or the guide wall.

One or more (and preferably all) of the funnel, the guide wall and the baffle wall are preferably suspended inside the three phase separator. Preferably one or more (and preferably all) of the funnel, the guide wall and the baffle wall are attached to the outer wall of the three phase separator, e.g. using struts.

An embodiment of the invention will now be described, by way of example only, with reference to the accompanying drawings, in which.

Up-flow anaerobic sludge blanket (UASB) reactors, treat waste water (e.g. produced in chemical and pharmaceutical industries) by anaerobically digesting organic matter in the waste water input into the reactor (the influent) using anaerobic micro-organisms that degrade the organic material. This produces an effluent of the reaction products containing, inter alia, methane ($CH_4$), carbon dioxide ($CO_2$), water ($H_2O$) and residual biomass solids ("sludge").

Figure 1:
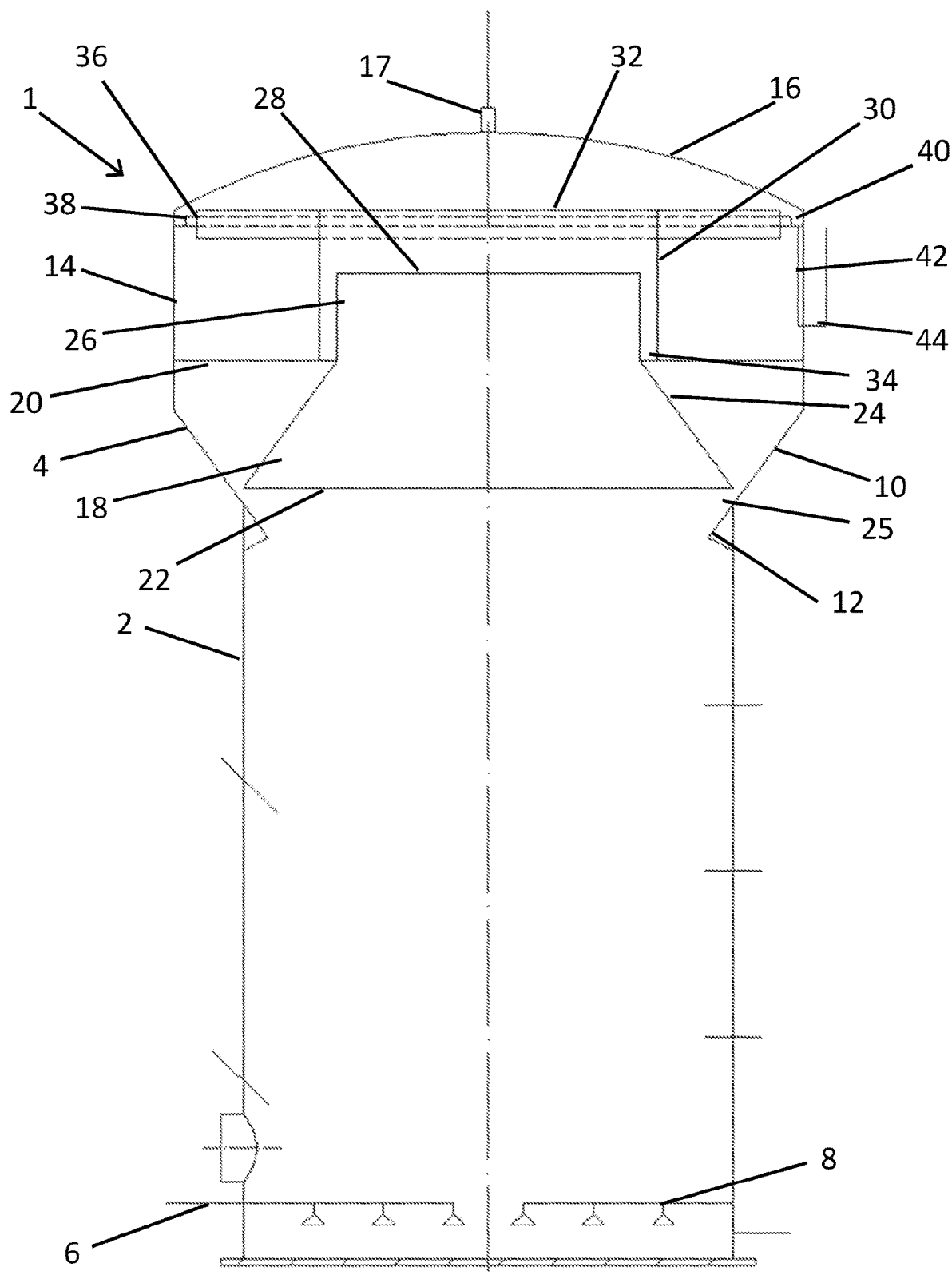
FIG. 1 shows a cross sectional view of an up-flow anaerobic sludge blanket reactor in accordance with an embodiment of the present invention.

FIG. 1 shows a cross sectional view of an up-flow anaerobic sludge blanket reactor 1 in accordance with an embodiment of the present invention. The reactor 1 includes a cylindrical reaction vessel 2 arranged below a three phase separator 4. The cylindrical reaction vessel 2 has an influent inlet 6 that inputs influent to be treated into the reaction vessel 2 through a plurality of distribution pipes 8. The reaction vessel 2 contains anaerobic micro-organisms that will anaerobically digest and thus degrade the organic matter in the influent fed into the reaction vessel 2.

Figure 2:
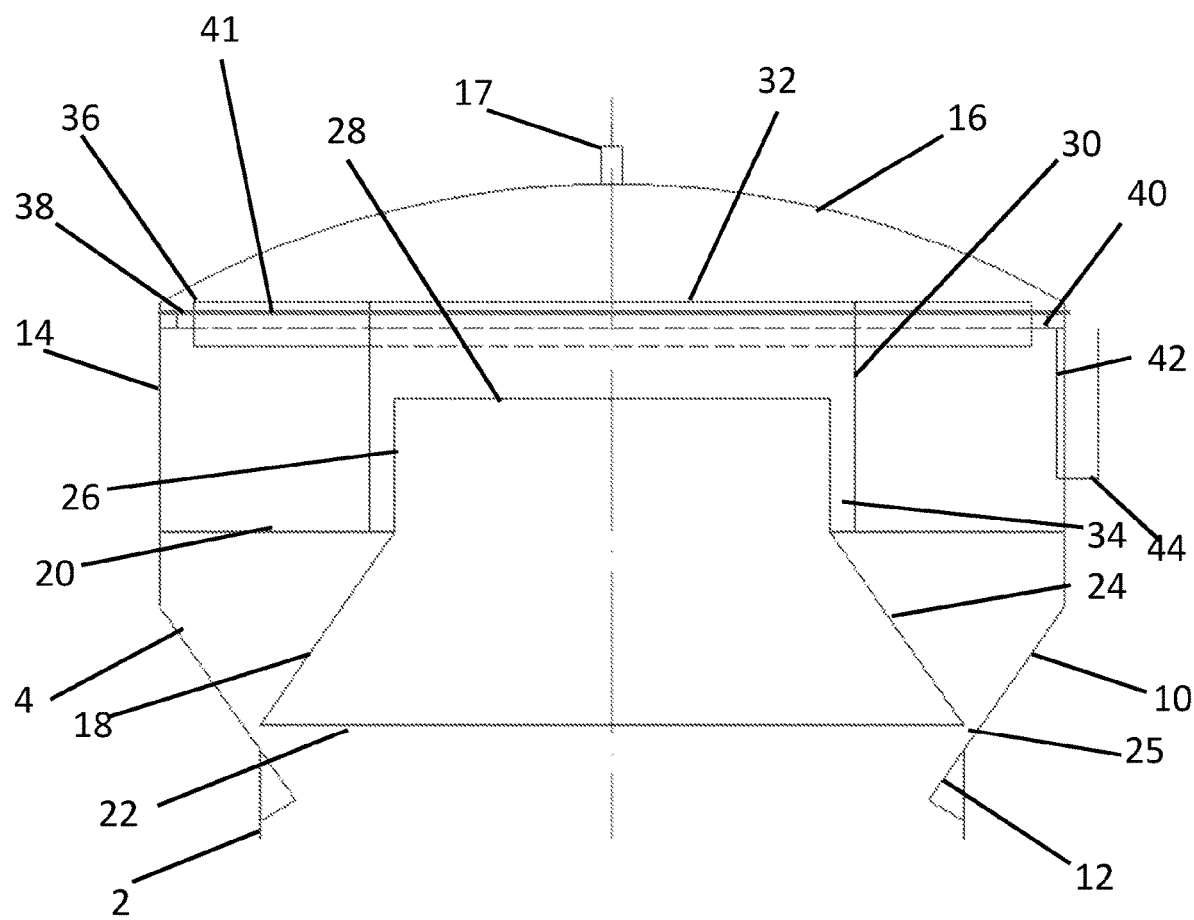
FIG. 2 shows the three phase separator of the reactor shown in FIG. 1.

FIG. 2 shows a close up cross sectional view of the three phase separator 4. As a whole, the three phase separator 4 is substantially rotationally symmetric and arranged coaxial with the reaction vessel 2, i.e. they share a common axis of rotation 9.

The three phase separator 4 is connected to the top of the reaction vessel 2, so that it receives the treated effluent (containing gas, liquid and solids) rising up from the reaction vessel 2. The three phase separator 4 has outer walls in a lower portion 10 that project outwards from the top of the reaction vessel 2 at an oblique angle. The projecting walls also extend inside the reaction vessel 2 to create an angled shelf 12 in the top of the reaction vessel 2.

The outer walls in an upper portion 14 of the three phase separator 4 are cylindrical, extending vertically between the lower portion 10 and a domed lid 16 that closes and substantially seals the top of the three phase separator 4. A gas outlet 17 is provided in the centre of the lid 16.

A funnel 18 is suspended by struts 20 inside the three phase separator 4. The funnel 18, that is rotationally symmetric and coaxially arranged with the reaction vessel 2, has a lower aperture 22 that is arranged above the reaction vessel 2. The lower aperture 22 of the funnel 18 forms the bottom of a conical lower portion 24 of the funnel 18. The lower aperture 22 also defines, with the walls of the lower portion 10 of the three phase separator 4, an annular conduit 25 that extends therebetween.

The funnel 18 has a cylindrical upper portion 26 whose walls extend vertically to an upper aperture 28. Arranged concentrically outward of the upper portion 26 of the funnel 18 is a cylindrical guide wall 30 that is also suspended by the struts 20 inside the three phase separator 4. The cylindrical guide wall 30 has an upper aperture 32 and together with the upper portion 26 of the funnel 18, the cylindrical guide wall 30 forms a lower annular aperture 34.

A vertically extending cylindrical baffle wall 36 is arranged concentrically outward of the guide wall 30. The top of the baffle wall 36 is level with the top of the guide wall 30. Concentrically outward of the baffle wall 36 is a liquid outlet wall 38 that forms a gutter 40 with the cylindrical outer wall of the three phase separator 4. The bottom of the baffle wall 36 extends below the top of the liquid outlet wall 38 and the top of the baffle wall 36 extends above the top of the liquid outlet wall 38.

A drain pipe 42 is arranged at the bottom of the gutter 40 to provide a liquid outlet for the liquid component of the effluent. A U-bend 44 is provided in the drain pipe 42 to prevent the escape of gas through the liquid outlet.

Figure 3:
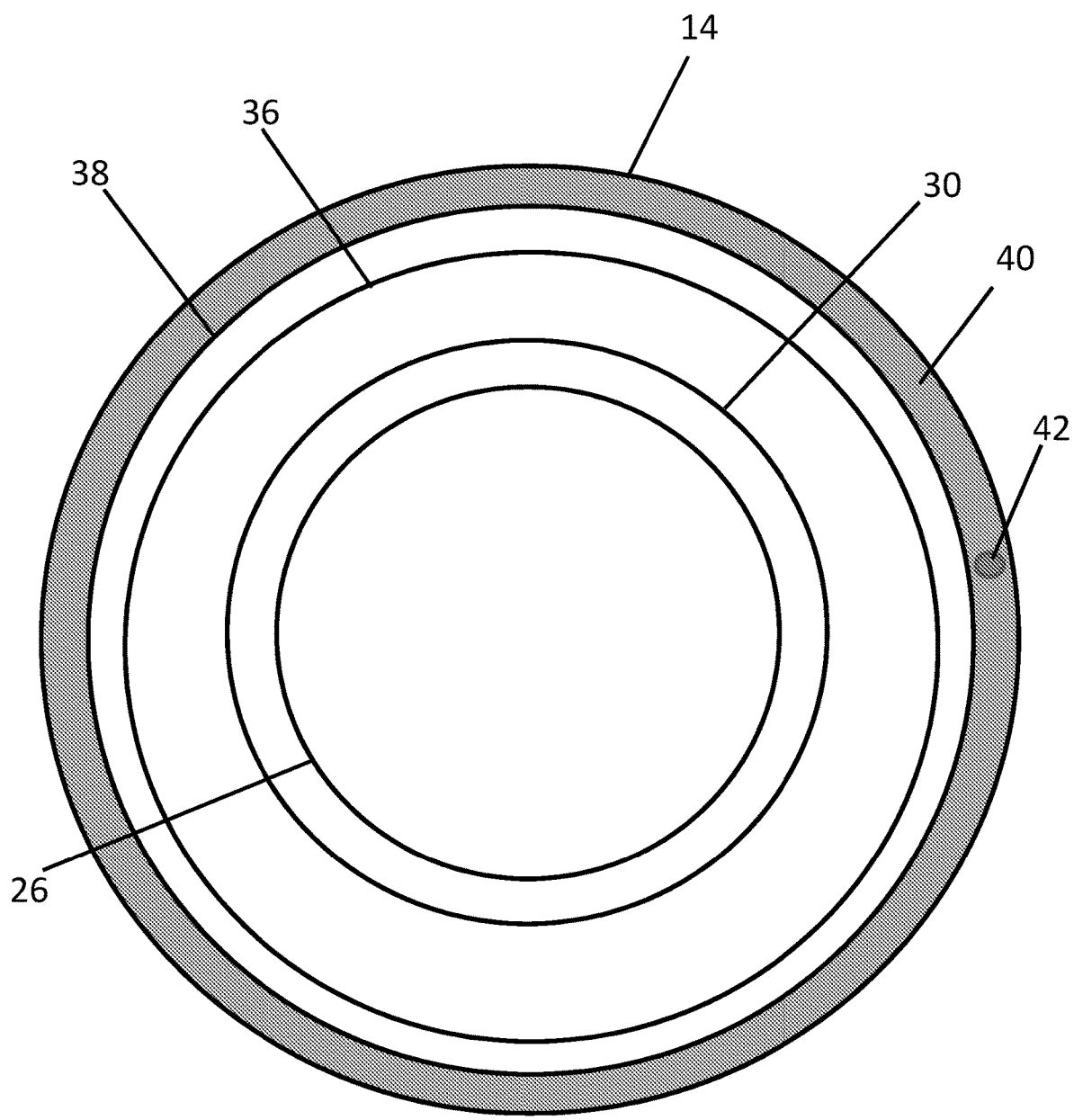
FIG. 3 shows a cross sectional view from above the three phase separator shown in FIG. 2.

FIG. 3 shows a cross sectional view from above the three phase separator 4 shown in FIG. 2. The concentric arrangement of the cylindrical upper portion 26 of the funnel 18, the cylindrical guide wall 30, the cylindrical baffle wall 36, the liquid outlet wall 38 and the cylindrical outer wall of the three phase separator 4, with the drain pipe 42 being arranged in the gutter 40, can be seen clearly from FIG. 3.

Figure 4:
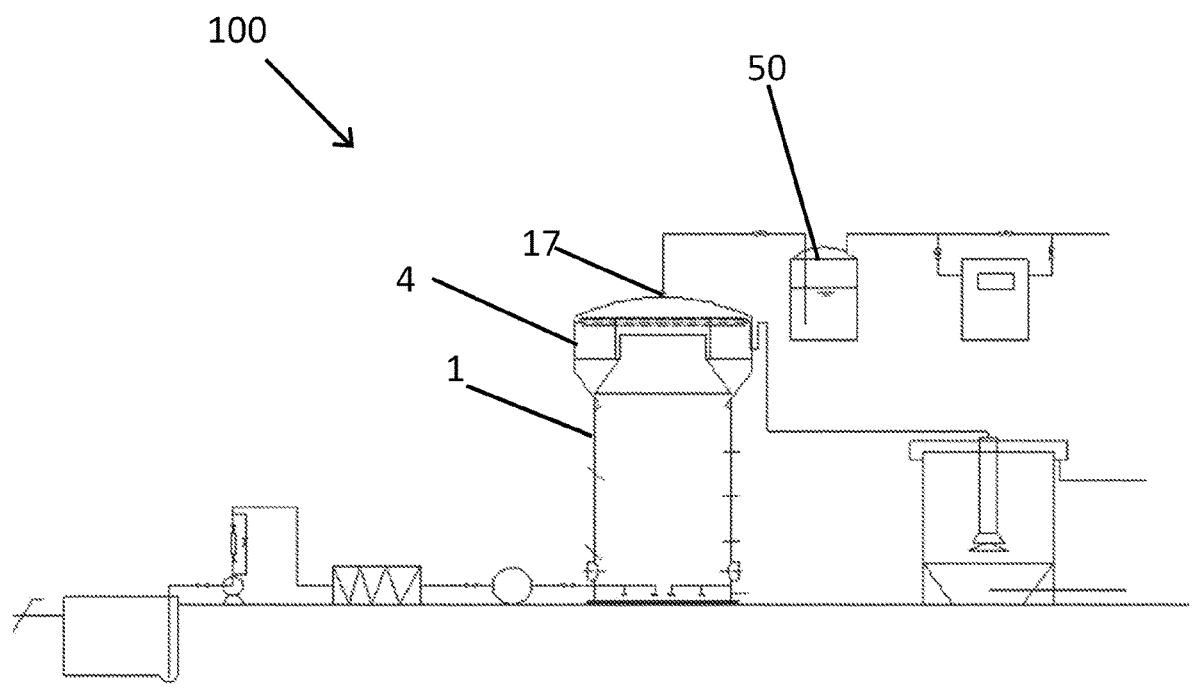
FIG. 4 shows an overview of a waste water treatment system including the reactor shown in FIG. 1.

FIG. 4 shows an overview of a waste water treatment system 100 including the reactor shown in FIG. 1. Downstream from the gas outlet 17 is a water sealing tank 50 that maintains a gas pressure in the three phase separator 4.

Figure 5:
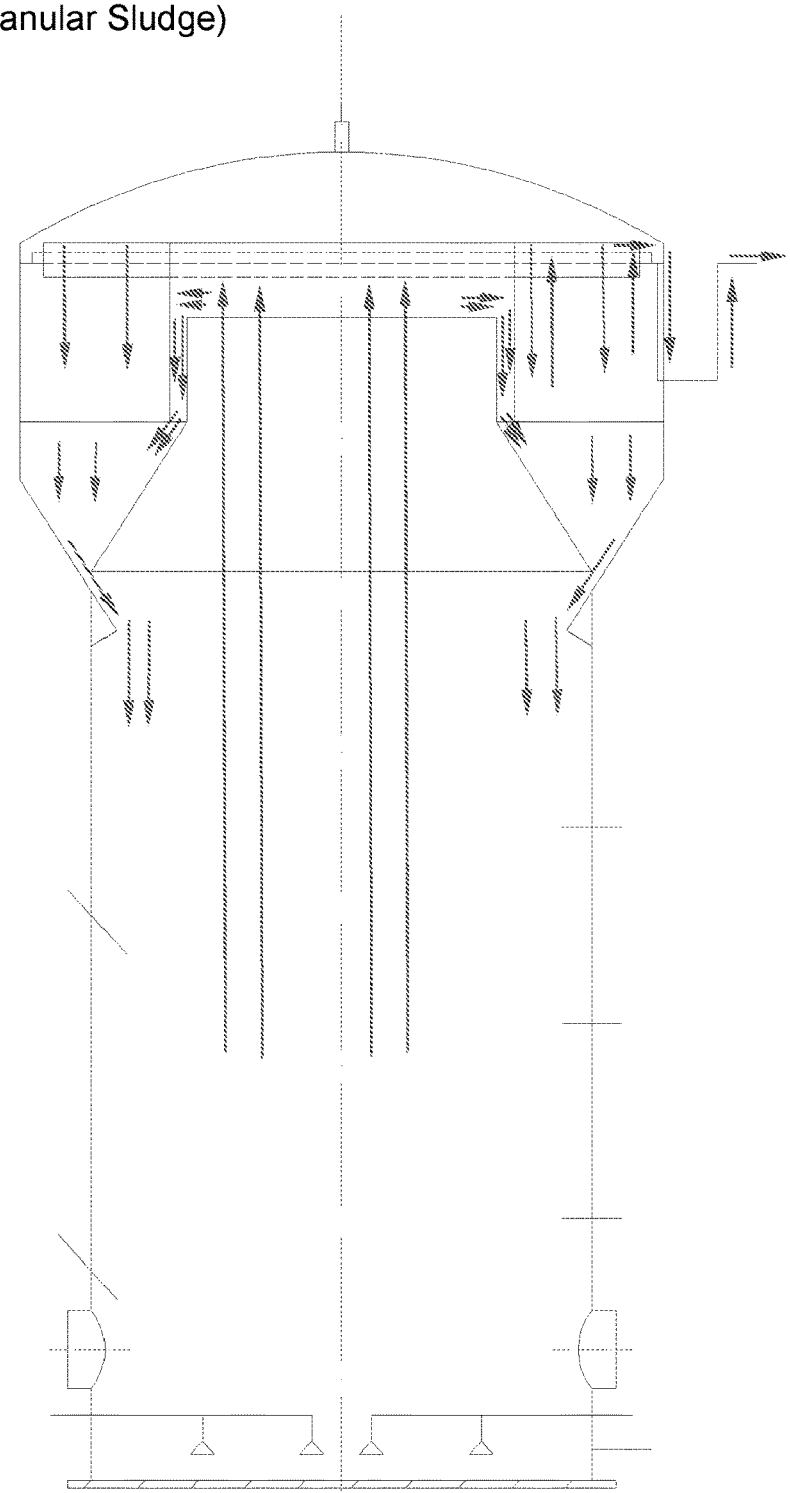
FIG. 5 shows the flow of influent and effluent through the reactor shown in FIG. 1.

FIG. 5 shows the flow of influent and effluent through the UASB reactor 1 shown in FIG. 1. Operation of the reactor 1 will now be described with reference to FIGS. 1-5.

Waste water containing organic matter, e.g. from a chemical or pharmaceutical industrial process, is input through the influent inlet 6 and enters the bottom of the reaction vessel 2 through the plurality of distribution pipes 8. The input of new waste water causes the influent already inside the reaction vessel 2 to rise up through the reaction vessel 2. The anaerobic micro-organisms in the reaction vessel cause the organic matter to be digested anaerobically.

The digestion process generates a large number of small gas bubbles that coalesce as they rise up through the reaction vessel 2. These growing bubbles, along with the flow of the liquid through the reaction vessel 2, convey the biomass solids (sludge) produced upwards within the reaction vessel 2. However, the sludge flocculates and/or granulates into larger agglomerations which then settle by gravity back down through the reaction vessel 2. The balance of the upward flow of liquid and bubbles, and the downward flow of flocculated and/or granulated sludge creates a layer ("blanket") of sludge in the reaction vessel 2 through which the influent flows. The blanket of sludge aids the anaerobic digestion of the influent flowing therethrough.

When the liquid reaches the top of the reaction vessel 2, the influent has largely been degraded into an effluent containing liquid (substantially water), gas (e.g. methane and carbon dioxide) and flocculated and/or granulated solids (biomass sludge). The three phase separator 4 is arranged to separate these components from each other, such that gas may be tapped off through the gas outlet 17, liquid may be output through the drain pipe 42 and the sludge may return to the reaction vessel 2.

The effluent first passes through the funnel 18 which guides the effluent into the cylindrical guide wall 30. The bubbles of gas in the effluent are guided by the cylindrical guide wall 30 towards the gas outlet 17. The liquid and sludge components of the effluent are prevented from flowing towards the gutter 40 by the top 32 of the cylindrical guide wall 30 that projects above the level of the liquid 41 in the three phase separator 4. The liquid and the sludge are therefore forced down through the lower annular aperture 34 between the cylindrical guide wall 30 and the upper portion 26 of the funnel 18.

Some of the sludge (e.g. the larger components) will fall down the outside of the lower portion 24 of the funnel 18 and will then pass through the annular conduit 25 between the lower aperture 22 of the funnel 18 and the walls of the lower portion 10 of the three phase separator 4. The remaining effluent that is outside of the funnel 18 and the cylindrical guide wall 30 still produces some gas bubbles that can rise to the surface and be captured by the lid 16 of the three phase separator 4 so that they can be tapped off through the gas outlet 17.

There will also be some lighter components of sludge that may be carried towards the liquid outlet gutter 40 but these are substantially prevented from doing so by the cylindrical baffle wall 36 that projects above the level of the liquid 41. The baffle wall 36 thus causes the remaining solids to flocculate and/or granulate such that they then fall back down the three phase separator 4 and back into the reaction vessel 2.

The liquid in the effluent is then able to flow under the baffle wall 36, over the top of the liquid outlet wall 38, into the gutter 40 and through the drain 42. The U-bend 44 in the drain pipe 42 prevents any gas from escaping through the liquid outlet.

The three phase separator 4 in accordance with the present invention thus provides effective separation of the liquid, gas and solids components in the effluent, as well as capturing substantially all of the gas that is produced by the anaerobic digestion.

Although the above embodiment has been described in the context of a UASB reactor, it will be appreciated that any type of anaerobic reactor requiring three phase separation may be used.

The invention claimed is:

1. An anaerobic reactor for treating waste water comprising:
    a reaction vessel comprising an inlet for supplying influent to be treated into the reaction vessel, wherein the reaction vessel is arranged to treat the influent received from the inlet using anaerobic digestion;
    a three phase separator arranged above, and in fluid communication with, the reaction vessel, wherein the three phase separator is arranged to receive effluent from the reaction vessel, wherein the effluent comprises solids, liquid, and gas;
    wherein the three phase separator comprises:
        an outer wall connected at its bottom to a top of the reaction vessel;
        a liquid outlet;
        a lid closing a top of the outer wall, wherein the lid comprises a gas outlet above a level of the liquid outlet;
        a funnel arranged above, and in fluid communication with, the reaction vessel, wherein the funnel comprises a lower aperture proximal to the reaction vessel and an upper aperture distal from the reaction vessel, wherein the lower aperture and the outer wall of the three phase separator or the top of the reaction vessel define an annular conduit therebetween, and the lower aperture has a cross sectional area that is greater than a cross sectional area of the upper aperture, and wherein the funnel comprises a wall that extends between the lower aperture and the upper aperture and is arranged to receive effluent from the reaction vessel and to guide the effluent from the lower aperture to the upper aperture, wherein the upper aperture is arranged below the level of the liquid outlet and the annular conduit is arranged to allow solids in the effluent to pass therethrough and fall back into the reaction vessel, wherein the funnel comprises a cylindrical upper portion and a conical lower portion;

a guide wall spaced from and arranged radially outward of the funnel to surround the upper aperture of the funnel, wherein a bottom of the guide wall aligns with a bottom of the cylindrical upper portion of the funnel and defines a lower annular aperture between the bottom of the guide wall and the wall of the funnel and the guide wall further defines an upper aperture arranged above the upper aperture of the funnel, wherein the guide wall is arranged to guide gas in the effluent from the funnel through the upper aperture of the guide wall towards the gas outlet, and the guide wall is arranged to allow solids and liquids in the effluent to pass through the lower annular aperture, wherein a radial distance between the guide wall and the upper portion of the funnel is less than a radial distance between the guide wall and the lower portion of the funnel, so that a settling area is defined between the lower portion of the funnel and the outer wall of the three phase separator; and a baffle wall spaced from and arranged between the guide wall and the liquid outlet, wherein a bottom of the baffle wall defines a lower aperture below the level of the liquid outlet and a top of the baffle wall defines an upper aperture above the level of the liquid outlet wherein, in use, the upper aperture of the baffle wall is above a liquid level in the three phase separator.

2. The anaerobic reactor as claimed in claim 1, wherein the anaerobic reactor comprises an up-flow anaerobic sludge blanket reactor.

3. The anaerobic reactor as claimed in claim 1, wherein the reaction vessel comprises a cylindrical body.

4. The anaerobic reactor as claimed in claim 1, wherein the inlet is provided towards a bottom of the reaction vessel.

5. The anaerobic reactor as claimed in claim 1, wherein the outer wall of the three phase separator is a continuous extension of an outer wall of the reaction vessel.

6. The anaerobic reactor as claimed in claim 1, wherein the outer wall of the three phase separator projects outwards from the top of the reaction vessel.

7. The anaerobic reactor as claimed in claim 1, wherein the liquid outlet comprises a liquid outlet wall between the baffle wall and the outer wall of the three phase separator.

8. The anaerobic reactor as claimed in claim 7, wherein the top of the liquid outlet wall is arranged to set the liquid level in the three phase separator.

9. The anaerobic reactor as claimed in claim 7, wherein the liquid outlet wall forms a trough comprising a drain through which liquid is arranged to flow out of the trough.

10. The anaerobic reactor as claimed in claim 7, wherein the top of the liquid outlet wall is lower than the top of the baffle wall.

11. The anaerobic reactor as claimed in claim 1, wherein the liquid outlet comprises a trap arranged to prevent gas from escaping through the liquid outlet.

12. The anaerobic reactor as claimed in claim 1, wherein the guide wall is cylindrical and extends vertically.

13. The anaerobic reactor as claimed in claim 1, wherein the upper aperture of the guide wall is arranged at the same level as the top of the baffle wall.

14. The anaerobic reactor as claimed in claim 1, wherein the baffle wall is positioned proximal to the outer wall of the three phase separator.

15. The anaerobic reactor as claimed in claim 1, wherein the baffle wall is cylindrical and extends vertically.

* * * * *